US012663211B2

(12) United States Patent
Choi

(10) Patent No.: US 12,663,211 B2
(45) Date of Patent: Jun. 23, 2026

(54) COCKPIT MODULE OF PURPOSE-BUILT VEHICLE

(71) Applicant: HYUNDAI MOBIS Co., Ltd., Seoul (KR)

(72) Inventor: Ik Keun Choi, Yongin-si (KR)

(73) Assignee: Hyundai Mobis Co., Ltd., Seoul (KR)

( * ) Notice: Subject to any disclaimer, the term of this patent is extended or adjusted under 35 U.S.C. 154(b) by 860 days.

(21) Appl. No.: 17/963,441

(22) Filed: Oct. 11, 2022

(65) Prior Publication Data

US 2023/0128258 A1     Apr. 27, 2023

(30) Foreign Application Priority Data

Oct. 22, 2021     (KR) ........................ 10-2021-0142128

(51) Int. Cl.
| | |
|---|---|
| *F26B 21/50* | (2026.01) |
| *A61L 2/10* | (2026.01) |
| *A61L 2/26* | (2006.01) |
| *B60H 1/24* | (2006.01) |
| *B60R 7/04* | (2006.01) |

(52) U.S. Cl.
CPC ............... *F26B 21/50* (2026.01); *A61L 2/10* (2013.01); *A61L 2/26* (2013.01); *B60H 1/24* (2013.01); *A61L 2202/11* (2013.01); *A61L 2202/121* (2013.01); *A61L 2202/122* (2013.01); *B60R 7/04* (2013.01)

(58) Field of Classification Search
CPC .......... F26B 21/004; F26B 3/28; F26B 3/283; F26B 3/04; F26B 9/003; F26B 19/005; F26B 25/16; F26B 21/50; A61L 2/10; A61L 2/26; A61L 2202/11; A61L 2202/121; A61L 2202/122; A61L 2202/14; A61L 2202/16; B60H 1/24; B60H 1/00592; B60H 1/00271; B60H 2001/003; B60H 1/00564; B60H 3/0071; B60H 3/024; B60R 7/04; B60R 7/08
See application file for complete search history.

(56) References Cited

U.S. PATENT DOCUMENTS

2020/0398702 A1     12/2020   Prozzi et al.

FOREIGN PATENT DOCUMENTS

| | | | |
|---|---|---|---|
| KR | 10-2006-0051453 A | 5/2006 | |
| KR | 10-2009-0036703 A | 4/2009 | |
| KR | 20-2014-0000008 U | 1/2014 | |
| KR | 10-2187060 B1 | 12/2020 | |
| WO | WO-2004078499 A1 * | 9/2004 | ......... B60H 1/00592 |

OTHER PUBLICATIONS

Korean Office Action Issued on Sep. 10, 2025, in Counterpart Korean Patent Application No. 10-2021-0142128 (7 Pages in English, 7 Pages in Korean).

* cited by examiner

*Primary Examiner* — Jessica Yuen
(74) *Attorney, Agent, or Firm* — NSIP Law

(57) ABSTRACT

Disclosed are cockpit modules for vehicles. The cockpit modules include a crash pad having a predetermined accommodation space, and a drying box, connected to an air conditioner of the vehicle, configured with respect to the crash pad to be storable in the accommodation space of the crash pad. The drying box, when interlocked with the air conditioner, dries and sterilizes items stored therein according to settings associated with the drying box.

5 Claims, 20 Drawing Sheets

ECU — 12

AIR CONDITIONER — 130

CONNECTING DUCT — 142

FIXING MEMBER — 145

ECU — 12

AIR CONDITIONER — 130

CONNECTING DUCT — 142

FIXING MEMBER — 145

COCKPIT MODULE OF PURPOSE-BUILT VEHICLE

CROSS-REFERENCE TO RELATED APPLICATIONS

This application claims the benefit under 35 USC § 119(a) of Korean Patent Application No. 10-2021-0142128, filed on Oct. 22, 2021, the entire disclosure of which is incorporated herein by reference for all purposes.

BACKGROUND

1. Field

The present invention relates to a cockpit module of a purpose-built vehicle (PBV).

2. Description of Related Art

Generally, with the development of vehicles, cockpit structures in vehicles have gradually been diversified, and various types of cockpit modules are also provided for each vehicle according to the design of the vehicle.

Cockpit module are often provided to meet the needs of vehicle occupants (including a driver, a passenger, and a user) according to traveling environments or the purpose of each situation. However, since typical cockpit modules only provide a limited type of general structure, these modules leave a lot to be desired in terms of convenience.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, here is provided a cockpit module for a purpose-built vehicle. The module includes a crash pad having a predetermined accommodation space, and a drying box, connected to an air conditioner of the vehicle, configured with respect to the crash pad to be storable in the accommodation space of the crash pad. The drying box, when interlocked with the air conditioner, dries and sterilizes items stored therein according to settings associated with the drying box.

The drying box may include a storage part positioned within the accommodation space of the crash pad to accommodate the at least one item, a connecting duct configured to connect the storage part and the air conditioner, an ultraviolet (UV) lamp configured to support and sterilize the at least one item placed within the storage part so that the at least one item in the storage part is dried, and a cover configured to open or close the storage part.

The connecting duct may connect a cold and hot pipe branched from the air conditioner and the storage part so that cold and hot air is introduced into the storage part.

The UV lamp may irradiate light having any one wavelength of UV-A and UV-C within the storage part.

The cover may be hinge-connected to one side section of the storage part to rotate the storage part at a predetermined angle and open or close the storage part.

The cover may include a fixing member snap-fit-fastened to the other side section of the storage part.

In another general aspect, here is provided a cockpit module of for a purpose-built vehicle. The cockpit module includes a crash pad, and a drying box, within the crash pad and connected to an air conditioner of the vehicle, configured to dry and sterilize at least one item placed therein according to settings associated with the drying box. The drying box includes a holder configured to support the at least one item placed therein for drying, an elevating member configured to move the holder up or down according to a size of the at least one item supported by the holder, and an ultraviolet (UV) lamp configured to irradiate UV light toward the at least one item supported by the holder.

The UV lamp, included in the holder, may be configured to sterilize the at least one item by irradiating UV-A light toward the at least one item supported by the holder.

The UV lamp, included in the holder, may be configured to sterilize the at least one item by irradiating UV-C light toward the at least one item supported by the holder.

The UV lamp, separate from the holder, may be configured to sterilize the at least one item by irradiating UV-A light toward the at least one item built into an upper end of the drying box and supported by the holder.

The UV lamp, separate from the holder, may be configured to sterilize the at least one item by irradiating UV-C light toward the at least one item built into an upper end of the drying box and supported by the holder.

The elevating member may be configured to vertically adjust a position of the holder by an operation of a separate switch.

The drying box may also include a connecting duct that connects a cold and hot pipe branched from the air conditioner and the storage part so that cold and hot air is introduced into the storage part.

In another general aspect, here is provided a cockpit module for a vehicle. The module includes a crash pad with a predetermined accommodation space, and a drying box, within the crash pad and connected to an air conditioner of the vehicle, configured to dry and sterilize at least one item placed therein according to settings associated with the drying box. The drying box is moveable and may be selectively drawn into and drawn out between the accommodation space of the crash pad and an interior of the vehicle.

The drying box may include a storage part positioned within the accommodation space of the crash pad to accommodate the at least one item, a connecting duct that connects the storage part and the air conditioner, a holder that supports the at least one item placed in the storage part for drying, and movable between the storage part and the interior of the vehicle, and movable between the storage part and the interior of the vehicle, a guide rail that provides a sliding path of the holder, and an ultraviolet (UV) lamp that irradiates UV light toward the at least one item target supported by the holder.

The drying box may also include a cover hinge-connected to one side section of the storage part configured to rotate the storage part at a predetermined angle and open or close the storage part.

The cover may include a fixing member snap-fit-fastened to an other side section of the storage part.

The drying box may also include an elevating member that moves the guide rail up or down according to a size of the at least one item supported by the holder.

The UV lamp may be detachably connected within the holder.

The UV lamp, separate from the holder, may be configured to sterilize the at least one item by irradiating light having any one wavelength of UV-A and UV-C toward the at least one item built into an upper end of the storage part and supported by the holder.

Other features and aspects will be apparent from the following detailed description, the drawings, and the claims.

BRIEF DESCRIPTION OF THE DRAWINGS

FIG. 1 is a perspective view schematically showing a state of a vehicle with a cockpit module, according to one or more embodiments.

FIG. 2 is a cross-sectional view taken along line A-A shown in FIG. 1.

FIGS. 3 to 5 are structural relationship diagrams showing an example of a drying box, according to one or more embodiments.

FIGS. 6 and 7 are structural relationship diagrams showing an example of a drying box, according to one or more embodiments.

Figure 8:
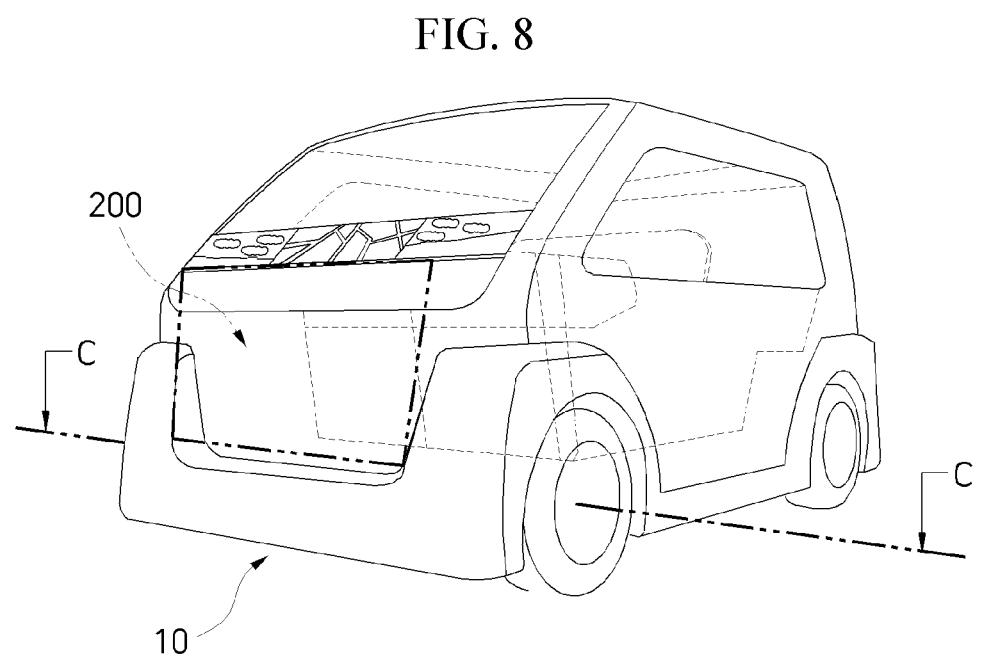

FIG. 8 is a perspective view schematically showing a state of a vehicle with a cockpit module, according to one or more embodiments.

FIG. 14 is a perspective view schematically showing a state of a vehicle with a cockpit module, according to one or more embodiments.

FIG. 15 is a cross-sectional view taken along line E-E shown in FIG. 14.

Figure 7:
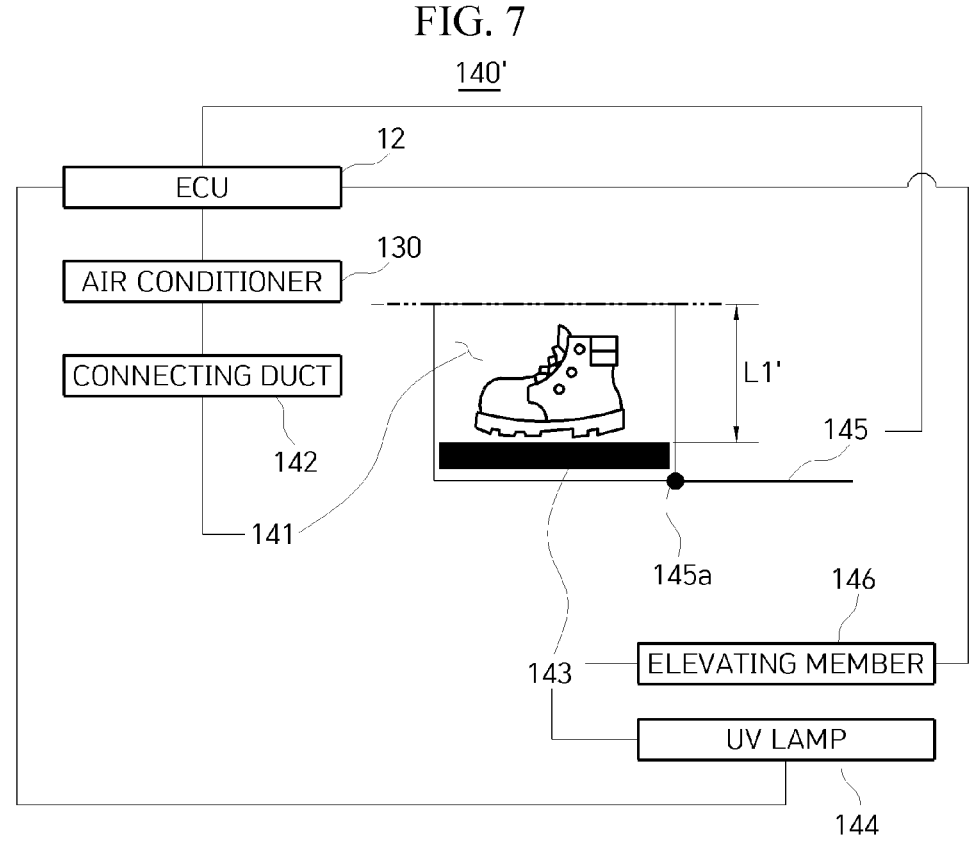

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order.

The features described herein may be embodied in different forms and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

The use of the term "up" or "upward" herein is meant to refer to a direction wherein a corresponding vehicle includes wheels on a lower portion of the vehicle compared to a roof of the vehicle in an upper portion of the vehicle.

Advantages and features of the present disclosure and methods of achieving the advantages and features will be clear with reference to embodiments described in detail below together with the accompanying drawings. However, the present disclosure is not limited to the embodiments disclosed herein but will be implemented in various forms. The embodiments of the present disclosure are provided so that the present disclosure is completely disclosed, and a person with ordinary skill in the art can fully understand the scope of the present disclosure. Meanwhile, the terms used in the present specification are for explaining the embodiments, not for limiting the present disclosure.

Terms, such as first, second, A, B, (a), (b) or the like, may be used herein to describe components. Each of these terminologies is not used to define an essence, order or sequence of a corresponding component but used merely to distinguish the corresponding component from other component(s). For example, a first component may be referred to as a second component, and similarly the second component may also be referred to as the first component.

Throughout the specification, when a component is described as being "connected to," or "coupled to" another component, it may be directly "connected to," or "coupled to" the other component, or there may be one or more other components intervening therebetween. In contrast, when an element is described as being "directly connected to," or "directly coupled to" another element, there can be no other elements intervening therebetween.

The singular forms "a", "an", and "the" are intended to include the plural forms as well, unless the context clearly indicates otherwise. It will be further understood that the terms "comprises/comprising" and/or "includes/including" when used herein, specify the presence of stated features, integers, steps, operations, elements, and/or components, but do not preclude the presence or addition of one or more other features, integers, steps, operations, elements, components and/or groups thereof.

Figure 1:
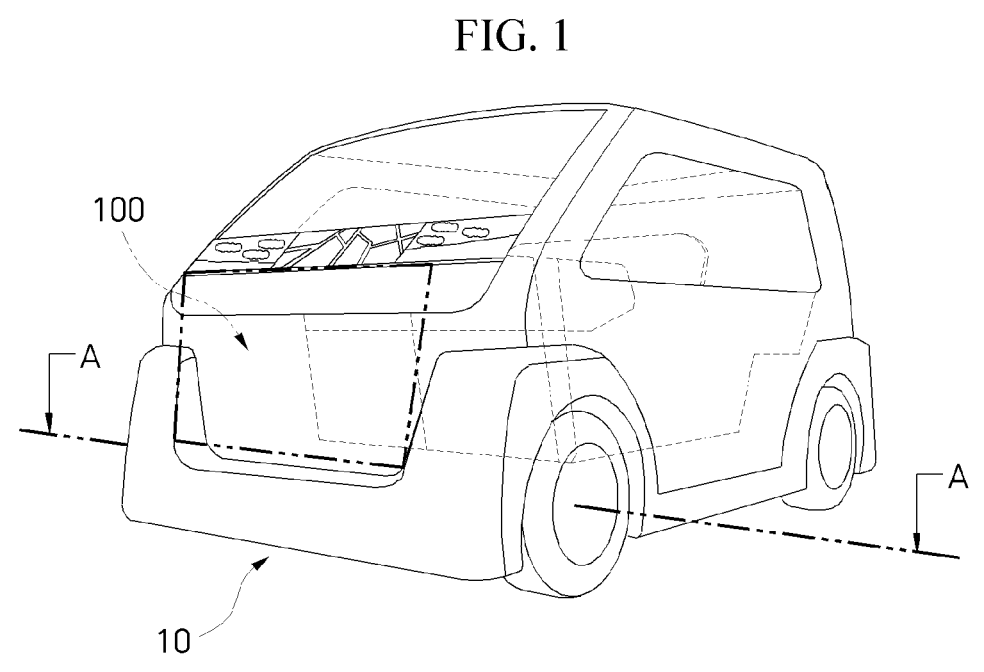

FIG. 1 is a perspective view schematically showing a state of a purpose-built vehicle in which a cockpit module according one or more embodiments.

Referring to FIG. 1, a purpose-built vehicle 10 is evaluated as a future vehicle in that it may travel for each purpose according to a design and provides an autonomous traveling environment.

Figure 2:
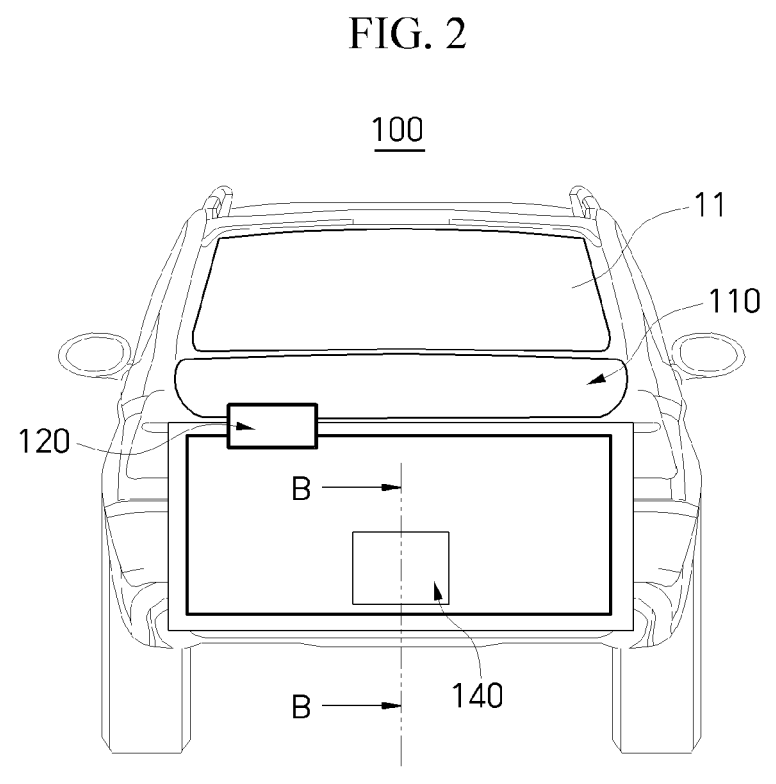

Examples exist with the purpose-built vehicle 10 having customized designs for various uses and convenience functions for autonomous traveling, and a cockpit module 100 may sterilize and dry occupants' items (e.g., shoes) through a drying box 140 (see FIG. 2).

FIG. 2 is a cross-sectional view taken along line A-A shown in FIG. 1.

Referring to FIG. 2, the cockpit module 100 includes a crash pad 110, a stowable column 120, and a drying box 140.

The crash pad 110 is an impact mitigating component for minimizing damage to occupants and a vehicle when the vehicle is in a collision and is positioned at a front portion of a vehicle body. The crash pad 110 has a predetermined accommodation space.

The stowable column 120 is connected to the crash pad 110 to carry out a steering function of the vehicle. The stowable column 120 may selectively be built into the crash pad 110.

For example, the stowable column 120 may have a structure in which a steering shaft is inserted into the crash pad 110, and a rim portion is folded toward the crash pad 110 (forward) or unfolded backward.

The drying box 140 may be stored in an accommodation space of the crash pad 110 in a state of being connected to an air conditioner 130 (e.g., FIG. 3) of the vehicle 10 (see FIG. 1). The drying box 140 may dry and sterilize separate targets (e.g., shoes, gloves, and other storage items) stored therein according to various settings in a state of being interlocked with the air conditioner.

Figure 3:
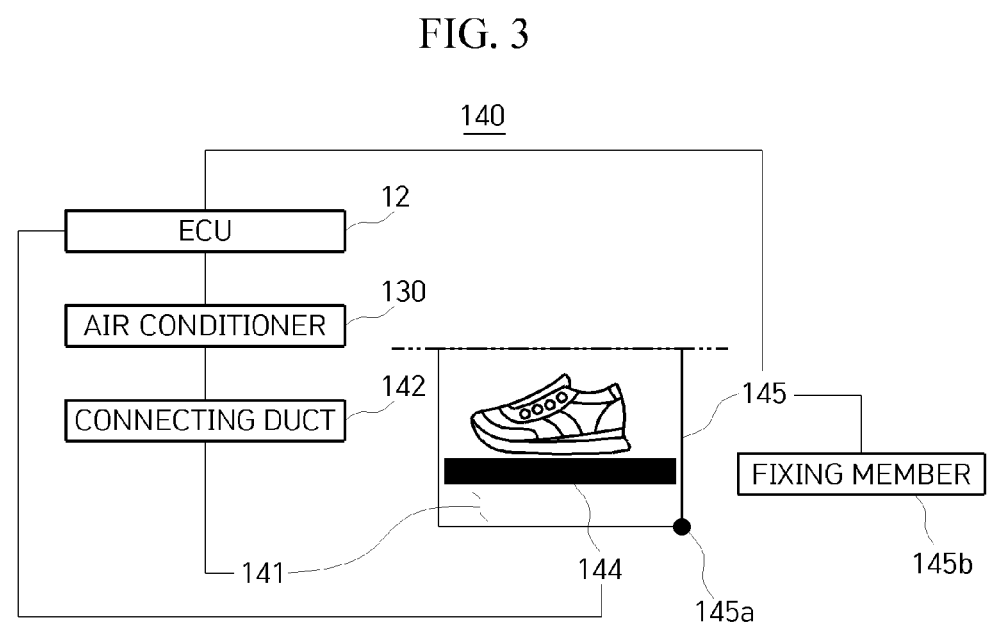
Figure 4:
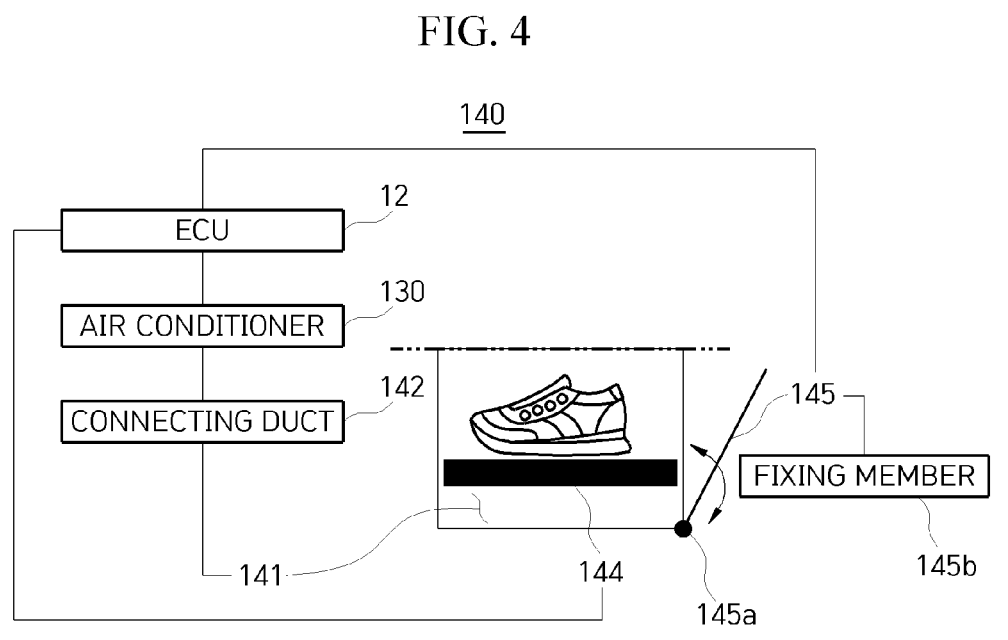
Figure 5:
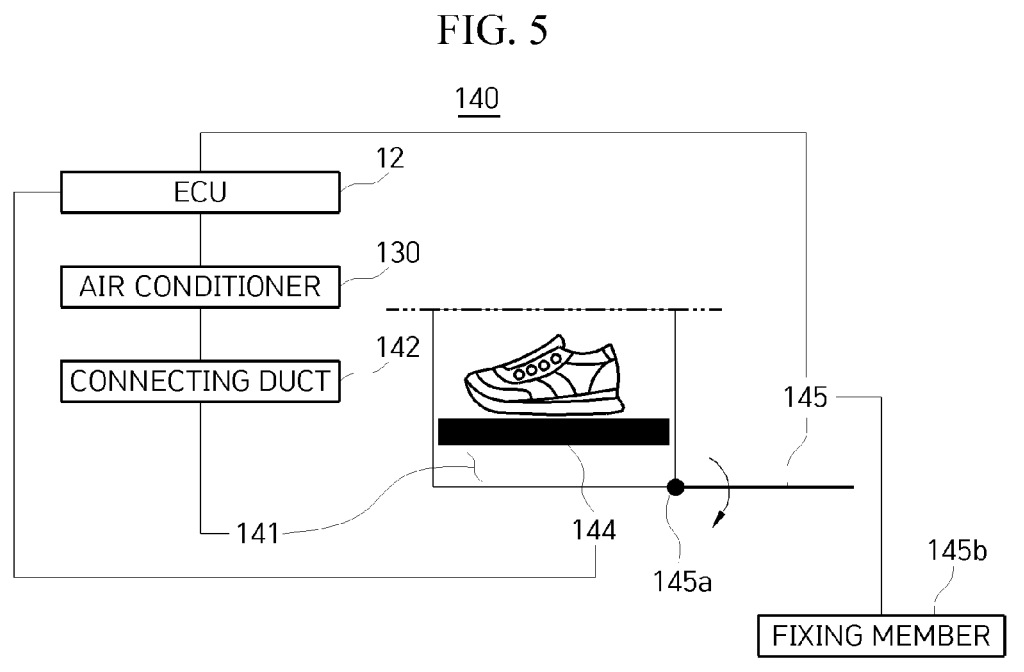

FIGS. 3 to 5 show an operation example of a drying box, e.g., based on a cross section taken along line B-B shown in FIG. 2 in the cockpit module.

Referring to FIGS. 3 to 5, the drying box 140 includes a storage part 141, a connecting duct 142, a UV lamp 144, and a cover 145.

The storage part 141 is positioned in the accommodation space of the crash pad 110. The storage part 141 has a separate storage space therein. Hereinafter, for convenience of description, the target to be stored in a storage space of the storage part 141 is specified as shoes, but this is only one example, and examples are not limited to shoes and may be various items that may be stored.

The connecting duct 142 connects the air conditioner 130 and the storage part 141. In other words, the connecting duct 142 connects a cold and hot pipe branched from the air conditioner 130 and the storage part 141 so that hot and cold air is introduced into the storage part 141 by an arbitrary operation. Here, an example operation may be a command representing one action of a user operating a separate controller (and/or switch) according to a situation as an example, and the corresponding command may be executed by an electronic control unit (ECU) 12 configured to control the entire system.

The UV lamp 144 functions as a holder by supporting shoes in a state of being positioned in the storage part 141 so that the shoes stored in the storage part 141 are dried. At the same time, the UV lamp 144 also sterilizes the shoes.

The UV lamp 144 may irradiate light having any one wavelength of UV-A and UV-C within the storage part 141. The UV-A refers to ultraviolet rays having a wavelength range of 315 to 400 nm, and the UV-C refers to ultraviolet rays having a wavelength range of 100 to 280 nm. Here, the UV-C may have the strongest sterilization force when it is about 254 nm.

As described above, the UV lamp 144 may effectively sterilize shoes by selectively adjusting the type and wavelength range of light.

The cover 145 opens or closes the storage part 141. The cover 145 may cover the air conditioner 130 hidden in the cockpit module 100 and the storage part 141 interlocked therewith. Accordingly, because the air conditioner 130 and the storage part 141 configured to store various items may be neatly covered by the cover 145, the occupant may recognize an interior of the vehicle as a neat and monotonous interior of the vehicle when viewed from the occupant's gaze of the purpose-built vehicle.

The cover 145 may be hinge-connected to one section of the storage part 141 by a hinge shaft 145a and opened or closed by rotating the storage part 141 at a predetermined angle.

The cover 145 may include a fixing member 145b that may be snap-fit-fastened to the other side section of the storage part 141.

Meanwhile, the drying box 140 may further include a water tank (not shown) connected to the storage part 141. The water tank may function as a water tank for absorbing moisture absorbed on the storage part 141 and discharge the absorbed moisture to the outside.

For example, the water tank may be detachably connected to the storage part 141 to discharge the absorbed moisture to the outside in a state of being separated or discharge the absorbed moisture to the outside through a separate discharge pipe.

Figure 6:
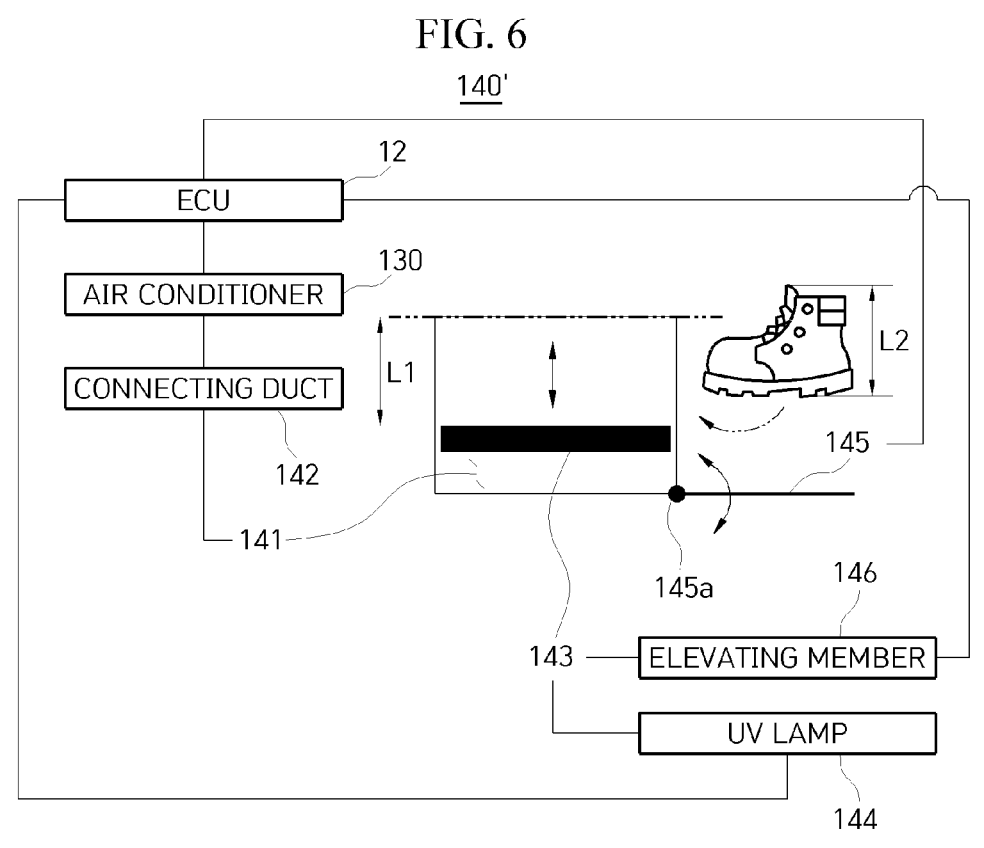

FIGS. 6 and 7 show an example of a drying box, e.g., based on a cross section taken along line B-B shown in FIG. 2 in the cockpit module.

Referring to FIGS. 6 and 7, a drying box 140' configures a separate holder 143 configured to hold shoes and includes an elevating member 146 configured to move the holder 143 up or down.

Here, it is characterized in that when a length L1 between an upper surface of the holder 143 and an upper end of the storage part 141 is shorter than a length L2 of a shoe, the drying box 140' vertically adjusts the holder 143 to an optimal length L1' at which the shoes may be accommodated through the elevating member 146.

The elevating member 146 may vertically adjust a position of the holder 143 by operating a separate switch.

The UV lamp 144 in the modified example of the first implementation may be built into the holder 143 or may irradiate UV light (UV-A or UV-C) for each type toward the shoes from the periphery of the holder 143.

At this time, the UV lamp 144 may sterilize the shoes by appropriately selecting the UV light for each type for each installation position.

FIGS. 8 to 11 show a cockpit module according to a second implementation of the present invention, and an operation example of a drying box among a detailed configuration thereof.

Referring to FIGS. 8 to 11, a cockpit module 200 has an opening mechanism of a drying box 240, e.g., different from the drying boxes 140 and 140'.

The drying box 240 may have a form built into an accommodation space of a crash pad 210.

The drying box 240 dries and sterilizes separate targets (e.g., shoes) stored therein according to arbitrary settings in a state of being connected to an air conditioner 230 of the vehicle within the crash pad 210.

The drying box 240 may have a feature that is selectively drawn into and out between the accommodation space of the crash pad 210 and an interior of the vehicle, and is movable.

To this end, the drying box 240 includes a storage part 241, a connecting duct 242, a holder 243, a UV lamp 244, a cover 245, and a guide rail 247.

The holder 243 supports the corresponding shoes stored in the storage part 241 to be dried, and is movable between the storage part 241 and the interior of the vehicle.

The UV lamp 244 may be detachably connected within the holder 243.

In particular, the UV lamp 244 is highly useful in that it is built into an upper end of the storage part 241 in a state of being spaced apart from the holder 243 and sterilizes the shoes by irradiating light having any one wavelength of UV-A and UV-C toward the shoes supported by the holder 243.

The guide rail 247 provides a sliding path of the holder 243.

The guide rail 247 may be positioned on an inner side end surface of the storage part 241 to support a lower portion of the holder 243.

There may also be provided a form in which a plurality of casters (not shown) are positioned between the holder 243 and the guide rail 247, or one belt is installed on an outer circumference of the guide rail 247 like a caterpillar, and a lower end surface of the holder 243 is connected to the belt.

Meanwhile, the drying box 240 may further include a water tank connected to the storage part 241 as well.

The corresponding water tank may function as a water tank for absorbing water absorbed on the storage part 241 and discharge the absorbed water to the outside.

For example, the water tank may have a structure that is detachably connected to the storage part 241 to discharge the absorbed moisture to the outside in a state of being separated or discharge the absorbed moisture to the outside through a separate discharge pipe.

Figure 9:
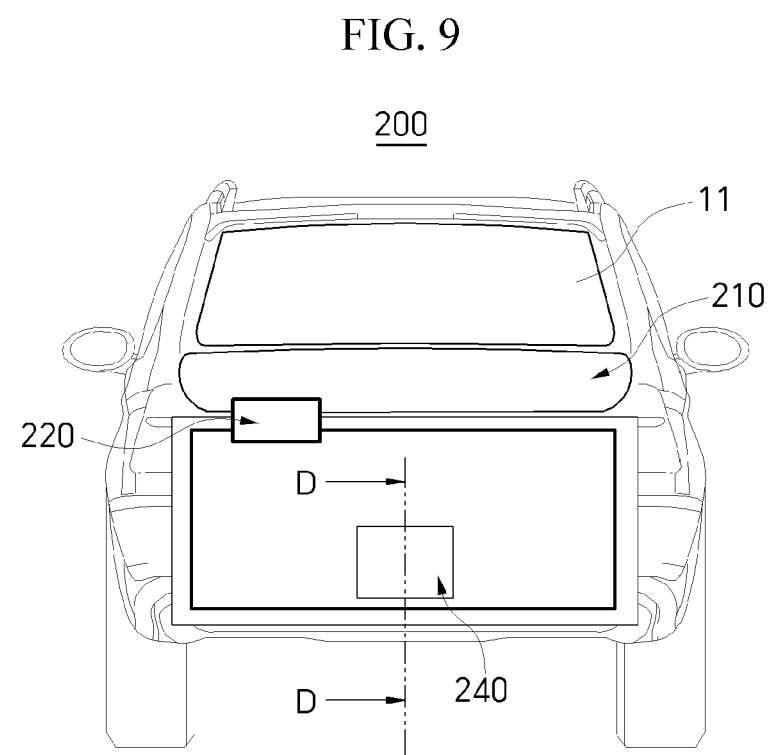
FIG. 9 is a cross-sectional view taken along line C-C shown in FIG. 8.
Figure 10:
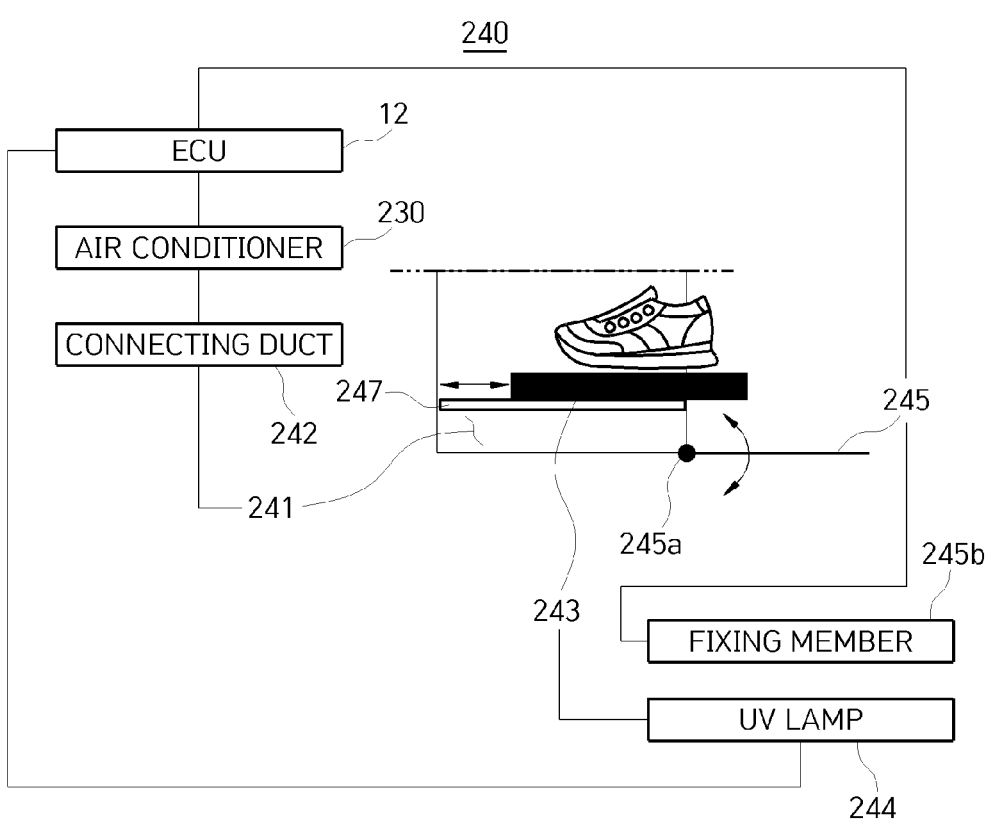
FIGS. 10 and 11 are structural relationship diagrams showing an example of a drying box, according to one or more embodiments.
Figure 11:
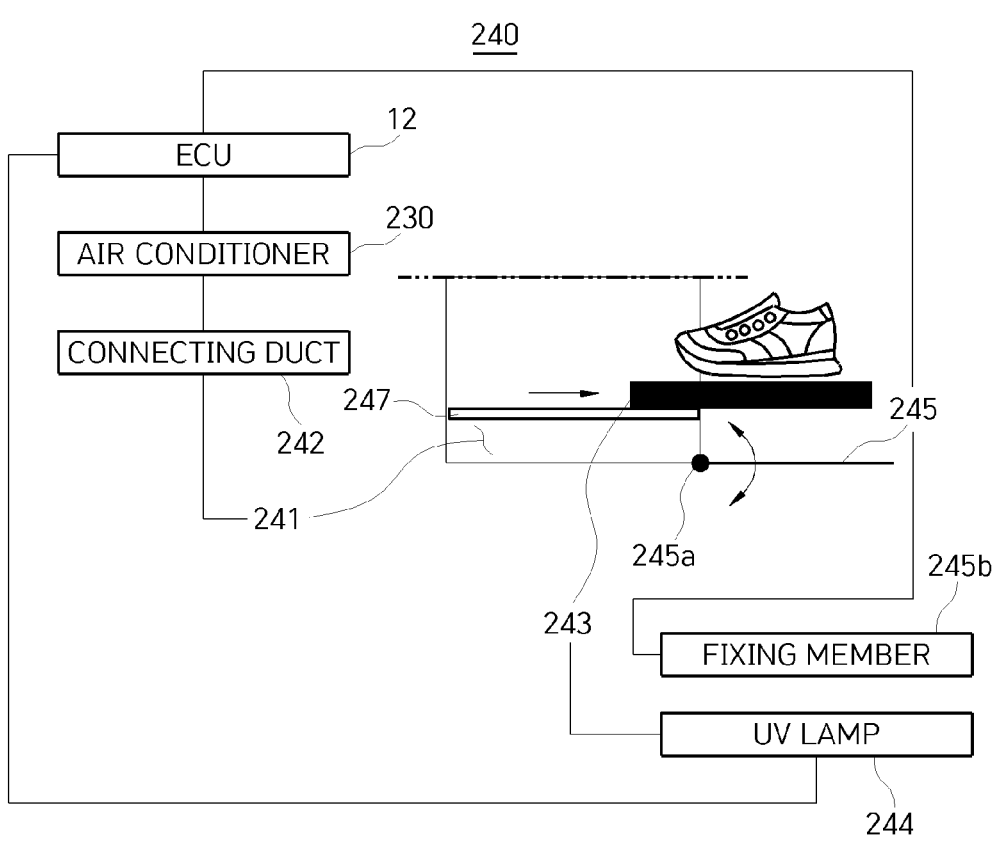
Figure 12:
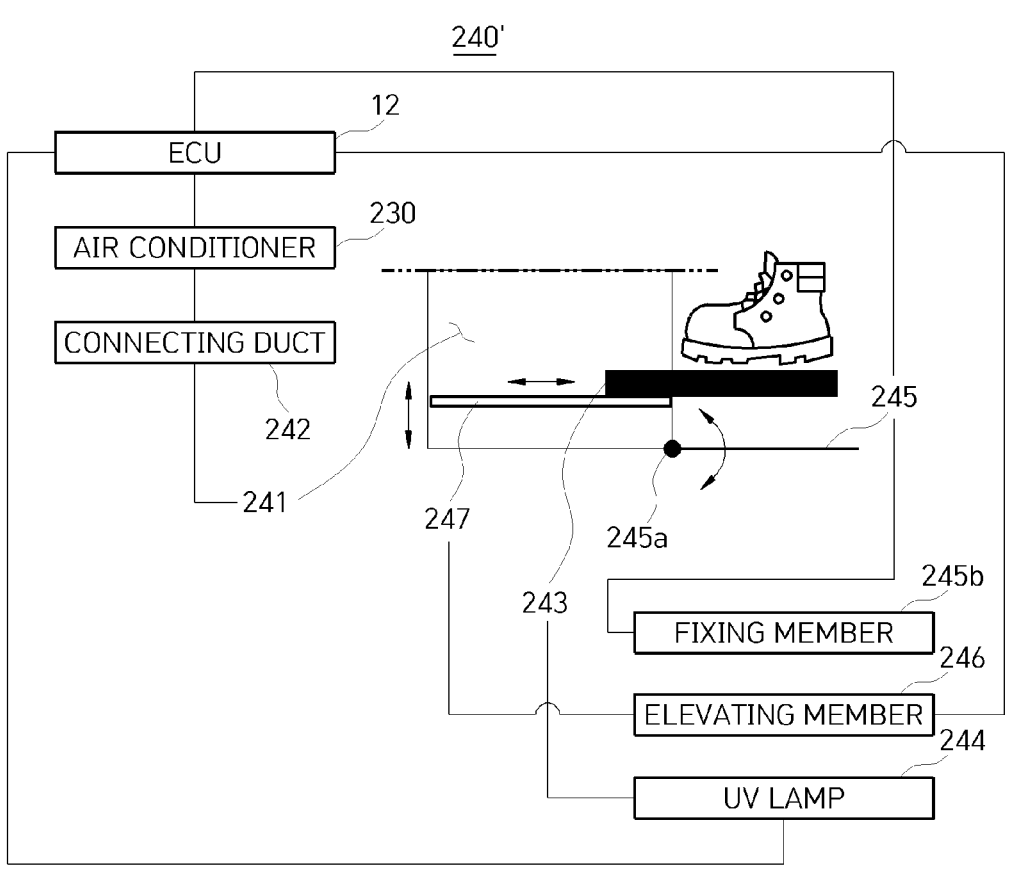
FIGS. 12 and 13 are structural relationship diagrams showing an example of a drying, according to one or more embodiments.
Figure 13:
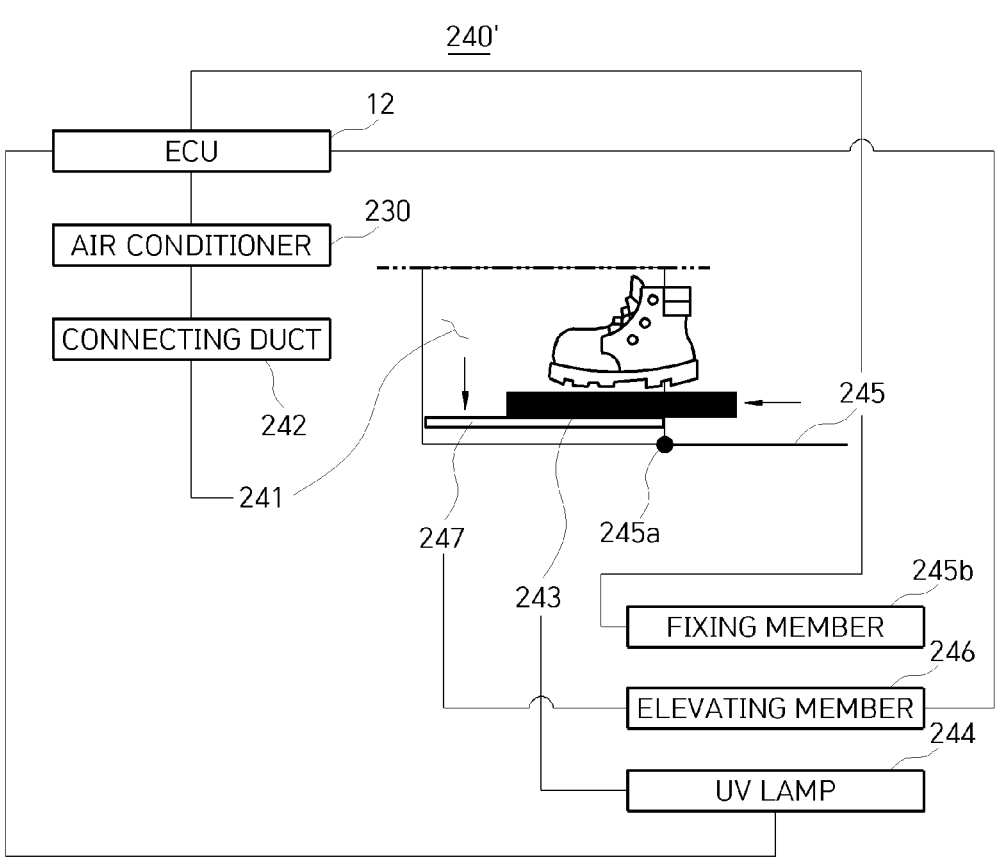

FIGS. 12 and 13 show an example of a drying box, e.g., based on a cross section taken along line D-D shown in FIG. 9 in the cockpit module.

Referring to FIGS. 12 and 13, a drying box 240' may further include an elevating member 246 configured to move the guide rail 247 up or down according to the sizes and/or heel lengths of the shoes supported by the holder 243.

Accordingly, shoes with a long heel may also be entered into and stored in the storage part 241 in a state of being supported by the holder 243.

The elevating member 246 connects an upper end and/or a lower end of the guide rail 247 to a side end of the storage part 241 to vertically move the guide rail 247 up or down according to a command of the ECU 12.

When the guide rail 247 moves up and down, the holder 243 interlocked with the guide rail 247 may move together because it is connected to the guide rail 247. A separate correction part for correcting a position of the guide rail 247 may be provided between the guide rail 247 and the side end of the storage part 241 so that the guide rail 247 may move up or down without shaking.

Discussions with respect to FIGS. 1-7 are also applicable to FIGS. 8-13 and thus overlapping descriptions will be omitted.

FIGS. 14 to 18 show a cockpit module implementation and an example drying box, according to one or more embodiments.

Figure 14:
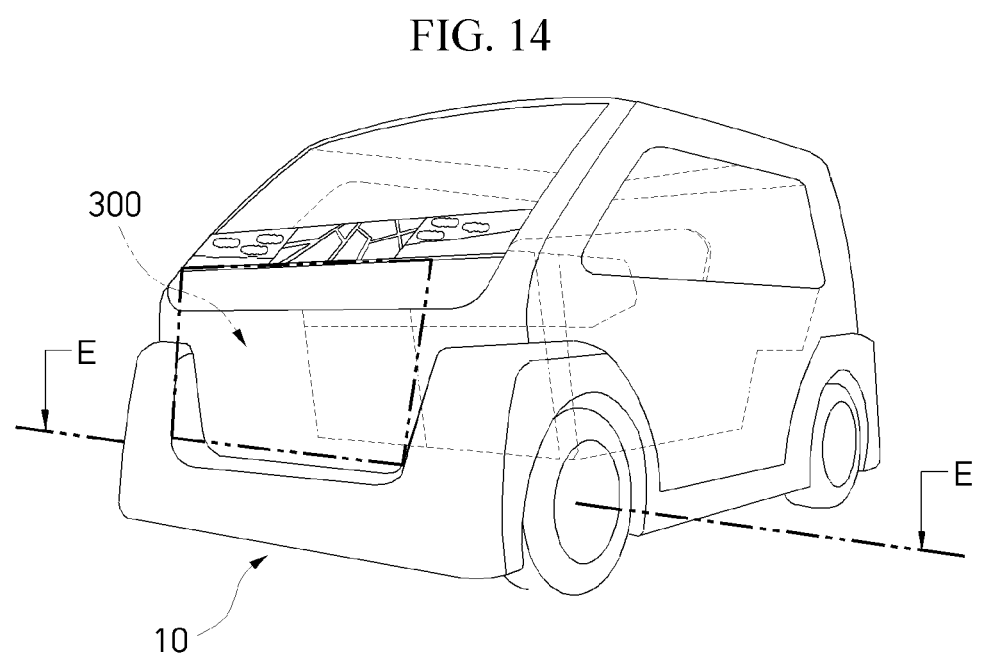
Figure 15:
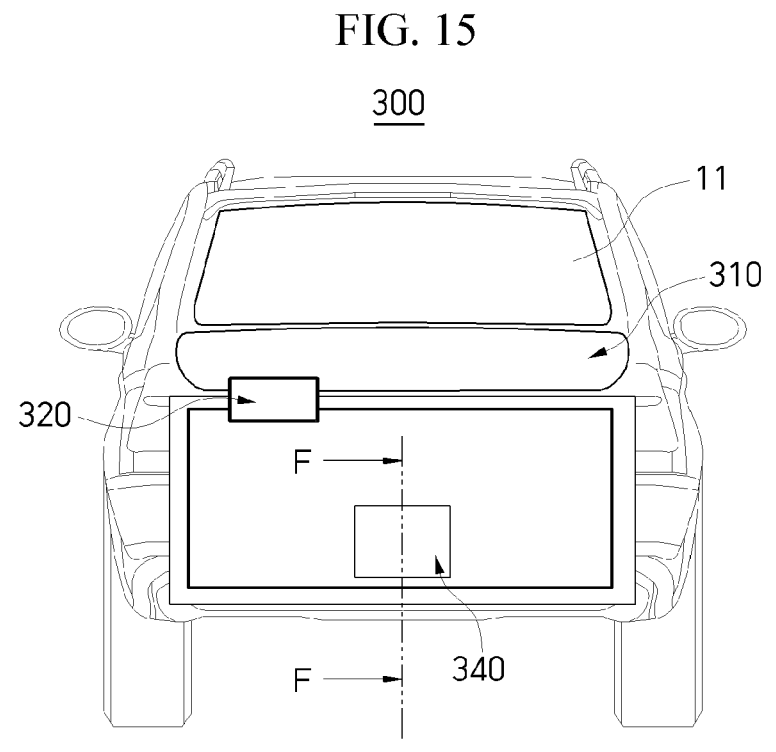
Figure 16:
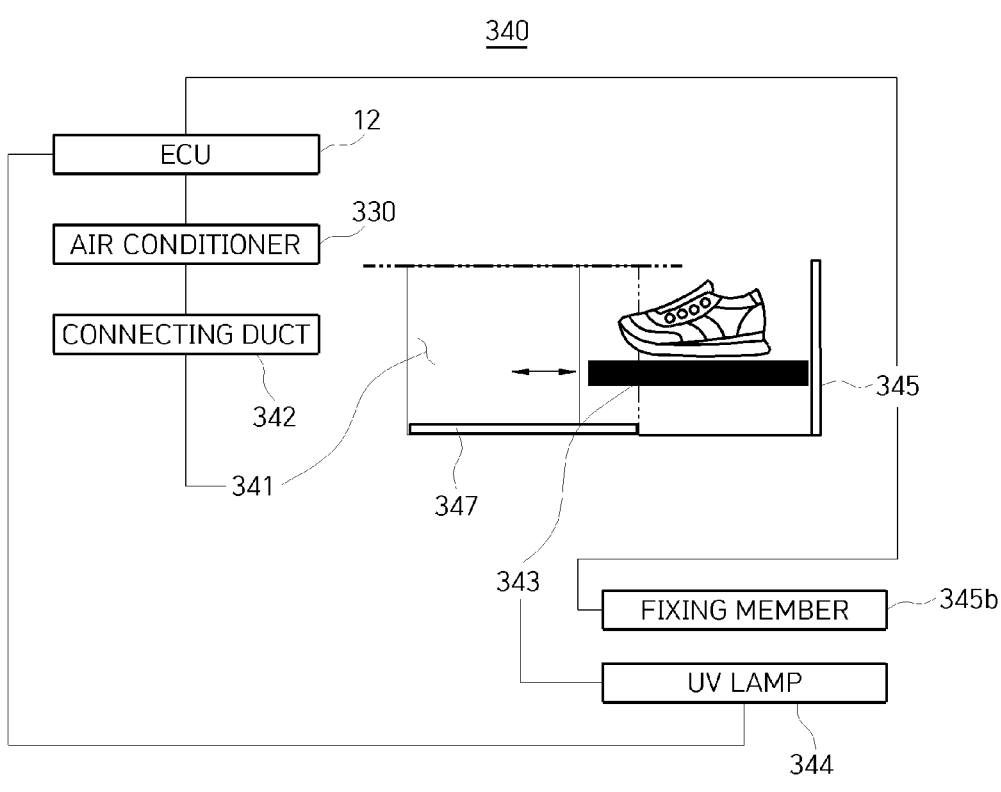
FIGS. 16 to 18 are structural relationship diagrams showing an example of a drying box, according to one or more embodiments.

Referring to FIGS. 14 to 16, a cockpit module 300 according to the third implementation provides a sliding mechanism (drawn into and drawn out) so that a user may easily store items (targets) in a drying box 340.

To this end, the drying box 340 may have a storage part 341 itself that is movable between an accommodation space of a crash pad 310 and an interior of the vehicle through a guide rail 347 disposed at a lower end.

Figure 17:
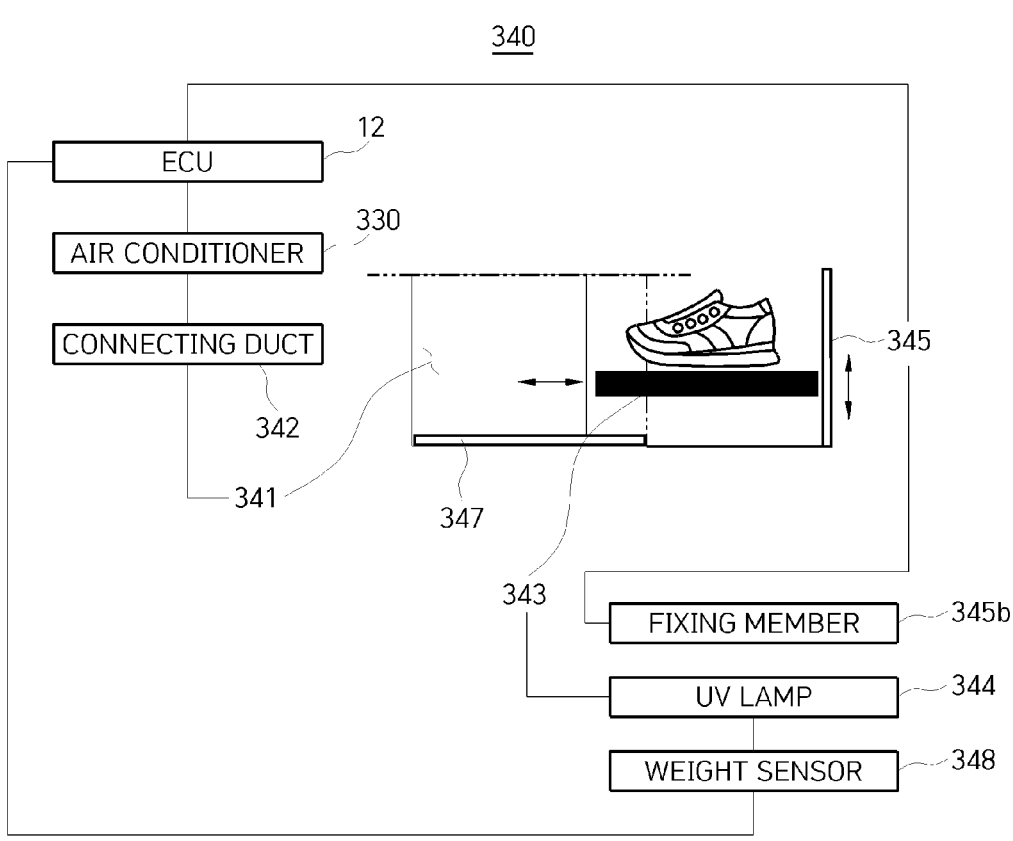
Figure 18:
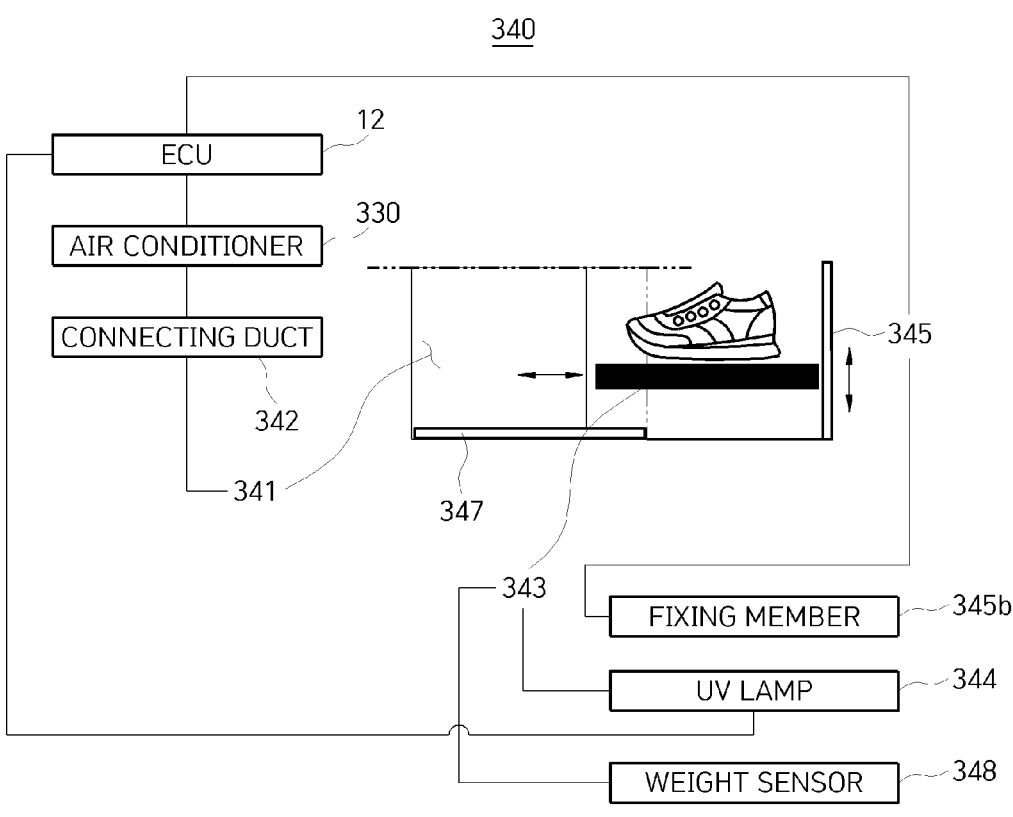

Referring to FIGS. 17 and 18, the drying box 340 may be implemented by changing a position at which an item is mounted or automatically adjusting drying and sterilization times according to the shape and weight of the item (target) stored in the drying box 340.

In other words, the drying box 340 implements a function of drying and sterilizing the corresponding item according to basic settings after comparing the corresponding item with information on a related item recorded in big data.

For example, in a state in which information on the weights and exposed contamination levels of the shoes supported by the holder 343 is stored in the big data in advance, the drying box 340 dries and sterilizes the corresponding shoes in order to set the shoes to an initial state after fetching information on the shoes from the big data.

Describing this process, when a weight sensor 348 detects the weights of the shoes supported by the holder 343, the weight sensor 348 transmits a corresponding detection information value to the ECU, and the ECU compares and calculates weight information received from the weight sensor 348 with reference information on the corresponding shoes fetched from the big data and then moves the holder 343 up or down according to the result values.

In addition, when the shoes are stored in the storage part 341, the ECU 12 turns on an air conditioner 330 to operate the UV lamp 344 in a state of introducing cold and hot air into the storage part 341 through the connecting duct 342 so that the shoes are dried and sterilized.

Figure 19:
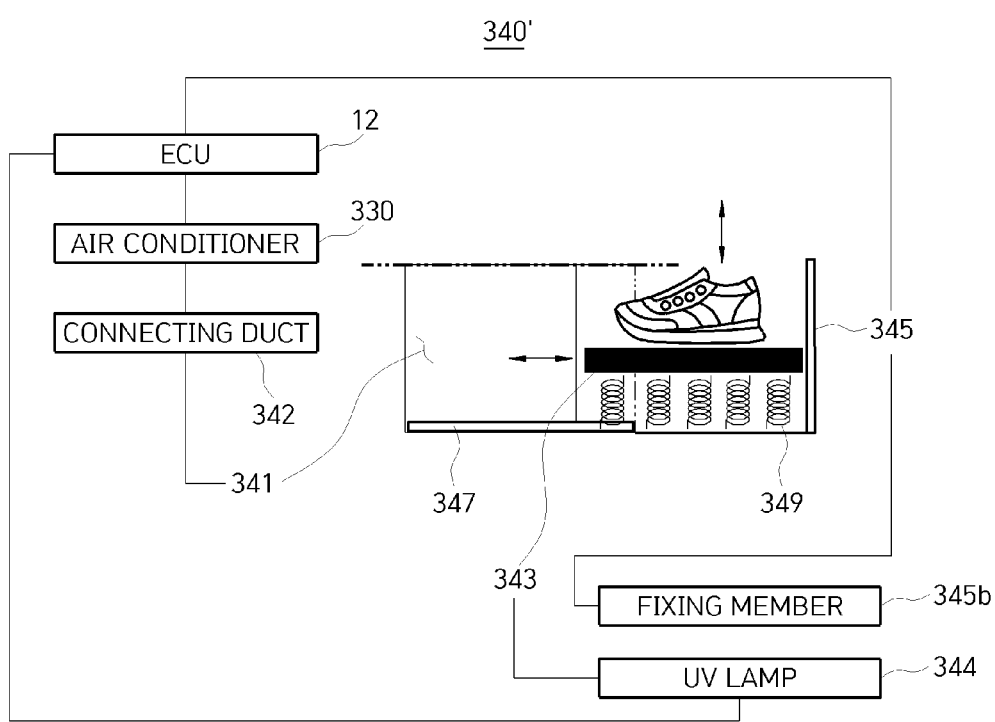
FIGS. 19 and 20 are structural relationship diagrams showing an example of a drying box, according to one or more embodiments.
Figure 20:
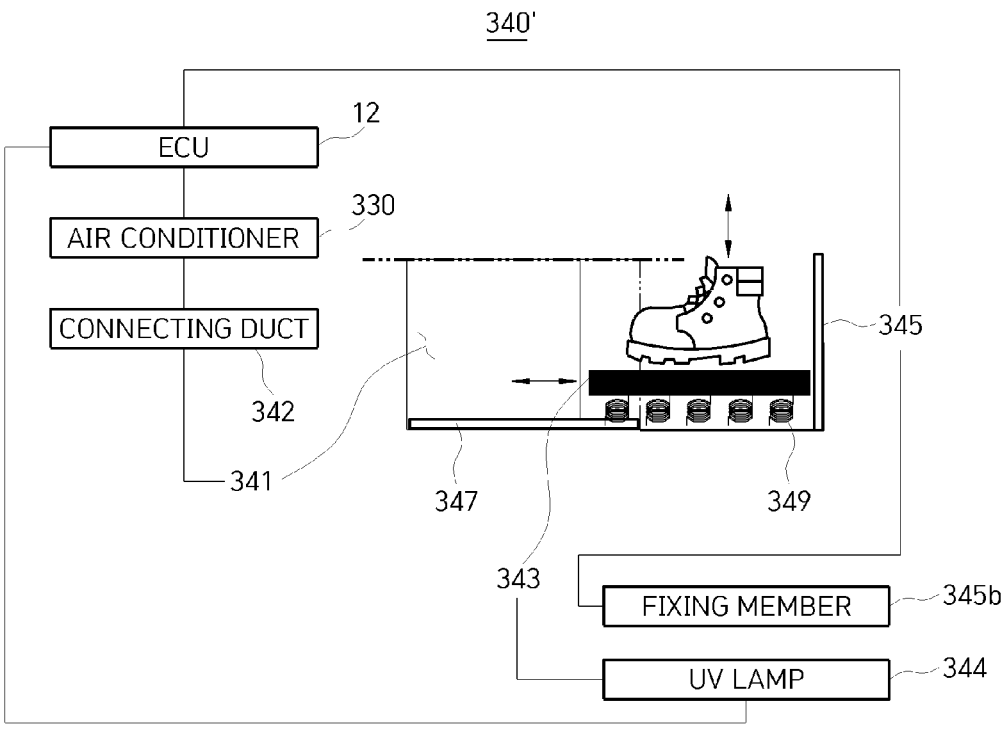

FIGS. 19 and 20 show an example of a drying box, e.g., based on a cross section taken along line F-F shown in FIG. 15 in the cockpit module.

Referring to FIGS. 19 and 20, when shoes exceeding the reference weight are mounted through an elastic member 349 disposed at the lower end, the holder 343 of the drying box 340' may be automatically moved up or down in connection with the weights of the corresponding shoes.

When the cover 345 is not drawn into the storage part 341 due to a length of the heels of the shoes in a state where holder 343 has moved down according to the weights of the shoes, the user may also change the position of the holder 343 by manually operating a separate switch.

The UV lamp 344 may irradiate UV light for each type toward the shoes supported by the holder 343 in a state of being built into the holder 343 or built into a plurality of positions in the storage part 341.

The present disclosure includes solutions to problems in the related art, and may provide a cockpit module of a vehicle that can increase occupants' convenience through a drying box that enables drying and sterilization treatments by storing separate targets (e.g., shoes) in a state of being connected to a heating, ventilating & air conditioning (HVAC) system.

Examples of the present disclosure may also increase or maximize a user's convenience by sterilizing and drying targets stored in a drying box such as shoes through a UV lamp, and cold and hot air of an air conditioner.

What is claimed is:

1. A cockpit module for a vehicle, comprising:
   a crash pad having a predetermined accommodation space; and
   a drying box, connected to an air conditioner of the vehicle, configured with respect to the crash pad to be storable in the accommodation space of the crash pad,
   wherein the drying box, when interlocked with the air conditioner, is configured to dry and sterilize at least one item therein according to settings associated with the drying box, and
   wherein the drying box includes:
      a storage part positioned within the accommodation space of the crash pad to accommodate the at least one item;
      a connecting duct configured to connect the storage part and the air conditioner;
      an ultraviolet (UV) lamp configured to support and sterilize the at least one item placed within the storage part so that the at least one item in the storage part is dried; and
      a cover configured to open or close the storage part.

2. The cockpit module of claim 1, wherein the connecting duct is configured to connect a cold and hot pipe branched from the air conditioner and the storage part so that cold and hot air is introduced into the storage part.

3. The cockpit module of claim 1, wherein the UV lamp is configured to irradiate light having any one wavelength of UV-A and UV-C within the storage part.

4. The cockpit module of claim 1, wherein the cover is hinge-connected to one side section of the storage part to rotate the storage part at a predetermined angle and open or close the storage part.

5. The cockpit module of claim 4, wherein the cover includes a fixing member snap-fit-fastened to the other side section of the storage part.

\* \* \* \* \*